(12) United States Patent
Lofman et al.

(10) Patent No.: US 12,370,378 B2
(45) Date of Patent: Jul. 29, 2025

(54) METHOD OF GENERATING A RADIOTHERAPY TREATMENT PLAN FOR A PATIENT, A COMPUTER PROGRAM PRODUCT, AND A COMPUTER SYSTEM COMPRISING A MACHINE LEARNING SYSTEM

(71) Applicant: RaySearch Laboratories AB (Publ), Stockholm (SE)

(72) Inventors: Fredrik Lofman, Lidingo (SE); Hanna Gruselius, Bromma (SE); Giorgio Ruffa, Stockholm (SE); Marco Trincavelli, Alvsjo (SE)

(73) Assignee: Raysearch Laboratories AB (publ), Stockholm (SE)

( * ) Notice: Subject to any disclaimer, the term of this patent is extended or adjusted under 35 U.S.C. 154(b) by 190 days.

(21) Appl. No.: 17/995,585

(22) PCT Filed: Apr. 6, 2021

(86) PCT No.: PCT/EP2021/058867
§ 371 (c)(1),
(2) Date: Oct. 6, 2022

(87) PCT Pub. No.: WO2021/204764
PCT Pub. Date: Oct. 14, 2021

(65) Prior Publication Data
US 2023/0158334 A1 May 25, 2023

(30) Foreign Application Priority Data
Apr. 9, 2020 (EP) ..................................... 20168982

(51) Int. Cl.
*A61N 5/10* (2006.01)
*G16H 20/40* (2018.01)

(52) U.S. Cl.
CPC ............ *A61N 5/1031* (2013.01); *A61N 5/103* (2013.01); *A61N 5/1037* (2013.01); *G16H 20/40* (2018.01)

(58) Field of Classification Search
CPC ........ A61N 5/10; A61N 5/103; A61N 5/1031; A61N 5/1038; A61N 5/1039;
(Continued)

(56) References Cited

U.S. PATENT DOCUMENTS 6,546,073 B1 * 4/2003 Lee ...................... A61N 5/1031
378/65
7,046,762 B2 * 5/2006 Lee ...................... A61N 5/1031
378/65
(Continued)

FOREIGN PATENT DOCUMENTS

CN 109843377 A 6/2019
CN 110709136 A 1/2020
(Continued)

OTHER PUBLICATIONS

International Search Report & Written Opinion, European Patent Office, May 21, 2021, Rijswijk, Netherlands.
(Continued)

*Primary Examiner* — Allen C. Ho
(74) *Attorney, Agent, or Firm* — Noréns Patentbyrå AB

(57) ABSTRACT

A machine learning-based method of generating a radiotherapy treatment plan for a patient, comprises dose prediction and dose mimicking, wherein the dose prediction step involves using a machine learning system that has been trained to consider at least one optimality criterion related to physical or technical restrictions that will affect the delivery of the treatment plan. Thus, at least one of the factors that are normally taken into account in the dose mimicking step is introduced in the dose prediction step. The invention also
(Continued)

relates to a method of training such a machine learning system for use in radiotherapy treatment planning, a computer program product and a computer system.

14 Claims, 2 Drawing Sheets

(58) Field of Classification Search
CPC .......... A61N 2005/1041; A61N 5/1048; A61N 5/1049; A61N 2005/1052; A61N 5/1071
USPC .......................................................... 378/65
See application file for complete search history.

(56) References Cited

U.S. PATENT DOCUMENTS

| | | | | |
|---|---|---|---|---|
| 7,734,010 B2* | 6/2010 | Otto | ............... | A61N 5/1031 378/65 |
| 9,827,445 B2* | 11/2017 | Cordero Marcos | .... | G16H 20/40 |
| 10,507,337 B2* | 12/2019 | Willcut | ............... | A61N 5/1038 |
| 10,850,121 B2* | 12/2020 | Moore | ............... | A61N 5/1031 |
| 10,984,902 B2* | 4/2021 | Laaksonen | ............. | G16H 30/40 |
| 11,011,264 B2* | 5/2021 | Zankowski | ........... | A61N 5/1039 |
| 11,013,936 B2* | 5/2021 | Cordero Marcos | .. | A61N 5/1039 |
| 11,020,615 B2* | 6/2021 | Eriksson | ............. | A61N 5/1031 |
| 11,071,877 B2* | 7/2021 | Zhou | ............... | A61N 5/1031 |
| 11,097,128 B2* | 8/2021 | Sjölund | ............... | G06N 3/084 |
| 11,291,856 B2* | 4/2022 | Eriksson | ............. | A61N 5/1036 |
| 11,358,003 B2* | 6/2022 | Sjölund | ............... | A61N 5/1081 |
| 11,367,520 B2* | 6/2022 | Sjölund | ............... | G16H 50/20 |
| 11,410,766 B2* | 8/2022 | Schreier | ............. | A61N 5/1038 |
| 11,475,991 B2* | 10/2022 | Laaksonen | ............ | G16H 20/40 |
| 11,517,768 B2* | 12/2022 | Hibbard | ............... | G06N 3/04 |
| 11,557,390 B2* | 1/2023 | Hibbard | ............... | G16H 20/40 |
| 11,605,452 B2* | 3/2023 | Adler | ............... | G16H 20/40 |
| 11,651,848 B2* | 5/2023 | Kuusela | ............... | G16H 30/40 600/1 |
| 11,717,702 B2* | 8/2023 | Yuan | ............... | G06N 3/08 600/1 |
| 11,724,126 B2* | 8/2023 | Adelsheim | ........... | A61N 5/1081 600/1 |
| 11,806,551 B2* | 11/2023 | Yang | ............... | G06F 17/18 |
| 11,842,498 B2* | 12/2023 | Laaksonen | ........... | A61N 5/1038 |
| 11,850,445 B2* | 12/2023 | Hibbard | ............... | A61N 5/1031 |
| 11,931,599 B2* | 3/2024 | Holmstrom | ........... | G16H 20/40 |
| 11,969,283 B2* | 4/2024 | Siversson | ............. | G16H 30/40 |
| 11,992,702 B2* | 5/2024 | Hibbard | ............... | G16H 50/20 |
| 2004/0165696 A1 | 8/2004 | Lee | | |
| 2006/0256915 A1 | 11/2006 | Otto et al. | | |
| 2019/0074079 A1 | 3/2019 | Zankowski et al. | | |
| 2019/0076671 A1 | 3/2019 | Willcut et al. | | |
| 2019/0111280 A1 | 4/2019 | Eriksson et al. | | |
| 2019/0192880 A1 | 6/2019 | Hibbard | | |
| 2019/0336793 A1 | 11/2019 | Zhou et al. | | |

FOREIGN PATENT DOCUMENTS

| | | |
|---|---|---|
| EP | 3228356 A1 | 10/2017 |
| EP | 3628372 A1 | 4/2020 |
| EP | 3892328 A1 | 10/2021 |
| JP | 2019146964 A | 9/2019 |
| WO | 2019027924 A1 | 2/2019 |

OTHER PUBLICATIONS

Office Action dated Apr. 9, 2024 from Chinese Patent Office, China.
Office Action dated Oct. 23, 2024 in corresponding Japanese patent application No. 2022-554400, Japan Paent Office, Tokyo, Japan.
Office action dated Aug. 27, 2024 in corresponding Chinese application No. 202180019284.7, Chinese Patent Office, Beijing, China.

* cited by examiner

METHOD OF GENERATING A RADIOTHERAPY TREATMENT PLAN FOR A PATIENT, A COMPUTER PROGRAM PRODUCT, AND A COMPUTER SYSTEM COMPRISING A MACHINE LEARNING SYSTEM

TECHNICAL FIELD

The present invention relates to a method of producing a radiotherapy treatment plan and a method of training a machine learning system, and to a computer program product and a computer system

BACKGROUND

Treatment planning is an important part of preparing for radiotherapy treatment and to an increasing degree involves the use of machine-learning. In such cases it consists of two main stages: dose prediction for producing a desired dose distribution and dose mimicking for producing a deliverable and physically feasible treatment plan based on the desired dose. These two stages are performed completely independently of each other.

Dose prediction may be machine learning based and produces a desired spatial dose distribution adapted to the patient geometry, according to a model that has been learned from a dataset of delivered doses. Dose mimicking uses the desired dose distribution as input to an optimization process. This stage is typically computationally heavy and time-consuming. The optimization problem is designed to take into account optimality criteria including the machine constraints of the delivery system and the physicality of the radiation delivery process and typically some other optimality criteria to determine a treatment plan that will result in an optimal deliverable dose to the patient.

US patent publication No. 2019/0192880 A1 and EP publication 3 628 372 disclose machine learning based dose prediction methods in which the machine learning systems have been trained using training sets comprising image data and a desired result, being trained to minimize the difference between the output based on image data and the known desired result.

The resulting dose from the optimization usually deviates from the predicted dose distribution because of various optimality factors tailored to what is physically and technically possible, which are applied at the dose mimicking stage. If the resulting deliverable dose is not useful, it may be difficult to determine whether the error occurred in the dose prediction stage or the dose mimicking stage.

SUMMARY OF THE INVENTION

It is an object of the invention to enable faster and more reliable treatment planning using a machine learning system.

The invention relates to a computer-based method of generating a radiotherapy treatment plan for a patient, said plan comprising providing radiation to a patient from a radiation source, the method comprising the steps of
  dose prediction by using a machine learning system to generate a predicted dose distribution or a set of irradiation parameters that can be used to generate a dose prediction for the patient dependent on patient geometry, based on a medical image and structure data comprising at least one delineated structure of the patient;
  dose mimicking by using the predicted dose distribution and/or set of irradiation parameters to generate a deliverable treatment plan, wherein
  the dose prediction step involves using a machine learning system that has been trained to consider at least one optimality criterion related to physical or technical restrictions that will affect the delivery of the treatment plan.

The invention also relates to a method of training such a machine learning system training a machine learning system for use in radiotherapy treatment planning, comprising the steps of
  providing a set of input data related to a medical image of a patient, structure date comprising at least one delineated structure of the patient, and a desired dose distribution dependent on patient geometry, determined on the basis of the medical image, to a machine learning system,
  comparing the output from the machine learning system to the desired dose distribution and feeding the result of the comparison to the machine learning system,
  wherein the set of input data further comprises at least one optimality criterion related to physical or technical restrictions that will affect the delivery of the treatment plan, and the training comprises training the machine learning system to consider the at least one optimality criterion related to physical or technical restrictions that will affect the delivery of the treatment.

According to the invention at least one of the factors that are normally taken into account in the dose mimicking step is introduced in the dose prediction step. This is in contrast to prior art methods in which the dose prediction step is based only on patient geometry, whereas the physical and technical restrictions associated with the delivery process are not considered until the dose mimicking step. By considering at least some of these restrictions already in the dose prediction step, the planning method will return a predicted dose that is closer to a dose that can actually be delivered to the patient to produce the desired result, or a set of irradiation parameters that may be used to determine such a predicted dose. Preferably, the set of irradiation parameters comprises sufficient information to determine the predicted dose. As a result, the dose mimicking step can be made faster while also returning a dose that better matches the predicted dose.

In preferred embodiments, the machine learning system comprises a non-trainable layer based on a dose function for the patient and is arranged to output a fluence distribution for each beam, spot positions and weights for each beam and energy or a set of brachy seed positions and dwell times, depending on the type of radiotherapy, and/or a dose distribution.

In a preferred embodiment, the machine learning system is a neural network that has been designed to consider at least one technical constraint of a delivery system to be used when delivering the treatment as the optimality criterion.

The training of the machine-learning model preferably comprises refining an optimization process, wherein the optimization procedure is based on an optimization problem comprising an optimization function related to the at least one optimality criterion.

The method of the invention also reduces the number of factors that may cause the deliverable dose to deviate from the predicted dose distribution by ensuring that some of the factors that influence dose mimicking are also considered in the dose prediction step, thereby enabling easier evaluation of machine learning models. Also, the learning process can be constrained since only the space of physically feasible solutions has to be searched, which makes it possible to produce good generalizations based on fewer patients than with conventional systems.

In preferred embodiments, the at least one optimality criterion includes parameters related to the physicality of the delivery process, including the interaction of the patient's geometry and the properties of the radiation source and the output from the dose prediction step, is expressed as a dose distribution or a set of irradiation parameters, or both. This means that the properties of the radiation source, including the type of radiation, and the effect of the radiation on the patient's body, is considered in the dose prediction step. The at least one optimality criterion may instead, or in addition to this, include one or more of the technical constraints of the system used for delivering the radiotherapy, such as the machine constraints of a delivery system. This means that the predicted dose will be closer to something that can actually be delivered by the delivery system. In preferred embodiments, optimality criterion or criteria are included in the optimization problem in the form of at least one constraint related to the optimality criteria.

The method is applicable to conventional radiation therapy planning using external beams and also to brachytherapy. It may be used for photon-based treatment plans and for particle-based treatment plans including plans using protons, neutrons or charged ions such as carbon or helium ions.

In a first preferred embodiment, the factor that is taken into account in the dose mimicking step is the physicality of the delivery process, which will affect factors such as path loss. This is done by considering the mapping function from irradiation parameters to dose distribution, which for photon radiation therapy may be described by a dose matrix.

This embodiment takes into account that the process generating the dose is either a set of beams producing photons or ionized particles, or, in the case of brachytherapy, a source of radioactive material inside the body. Therefore, the dose will be distributed according to the laws of physics that govern the spreading of radiation into matter. This is to a great extent dependent on the properties of the parts of the patient's body affecting the radiation. As is well known, the irradiation is affected differently by passing through, water, air, bone, fat or other types of tissue.

In a second preferred embodiment, the factor that is taken into account in the dose mimicking step is the deliverability of the dose. This is done by considering the properties of the delivery system. In this way it can be ensured that the predicted dose is one that is deliverable with respect to the machine constraints.

Both factors, the geometry and the deliverability, may be considered together. Preferably, they are considered again in the dose mimicking step in the conventional way to ensure the best possible plan. This will be faster than in prior art systems because the deliverable dose that forms input data to dose mimicking is created taking the physicality and/or the machine constraints into account.

The invention also relates to a computer program product comprising computer readable code means which, when run in a computer, will cause the computer to perform the method of generating a radiotherapy treatment plan as discussed above. The invention also relates to a computer program product comprising computer readable code means which, when run in a computer, will cause the computer to perform the method of training a machine-learning model as discussed above. The computer program products may be stored on any type of suitable carrier, for example, a non-transitory carrier. The invention also relates to a computer system comprising a processor, a program memory and a data memory, wherein the program memory comprises one or both such computer program product.

BRIEF DESCRIPTION OF DRAWINGS

The invention will be described in more detail in the following, by way of examples and with reference to the appended drawings.

DETAILED DESCRIPTION OF EMBODIMENTS

Figure 1:
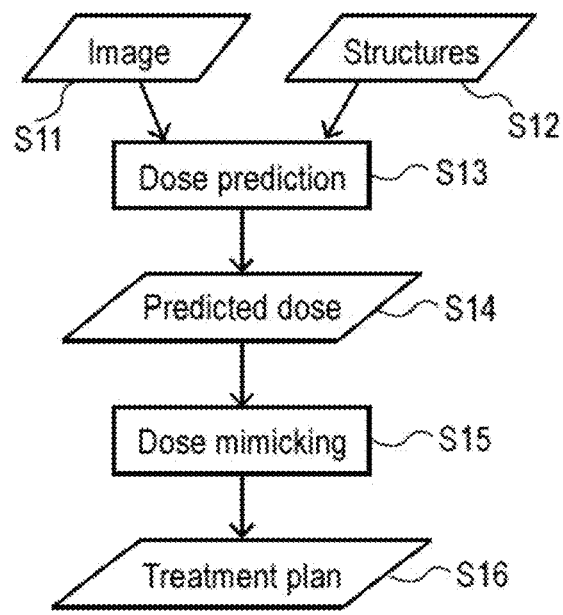
FIG. 1 is an overview of a procedure of dose prediction and dose mimicking.

FIG. 1 is an overview of a prior art method of dose prediction and dose mimicking. Input data to the procedure include at least one of a medical image S11 and structure data S12. The medical image S11 is a medical image of a portion of a patient, such as a CT image or an MR image. Structure data include delineated structures of the patients, of one or more regions of interest (ROI). These input data are used in a dose prediction step S13 that is performed in a machine learning system to generate a predicted dose which is a spatial dose adapted to the patient's geometry. The output from the dose prediction step S13 is a predicted dose S14, or a set of irradiation parameters that may be used in a subsequent step (not shown) to generate a predicted dose. The predicted dose S14 is used as input data to a dose mimicking step S15, which generates a deliverable treatment plan S16 for the patient. As is common in the art, the dose mimicking step S15 is designed to ensure that the treatment plan S16 comes as close as possible to producing the desired dose distribution, taking into account the actual physiological and technical conditions. This means that the dose mimicking step S15 is typically designed to enforce the following criteria:

the dose distribution resulting from the interaction of the irradiation with the patient tissue, taking the geometry and anatomy of the patient into account,
the physicality of the radiation source,
the deliverability of the plan with respect to the machine constraints of the delivery system that is to be used,
the optimality criteria with respect to the predicted dose,
other optimality criteria such as radiobiological effect (RBE).

The radiation source may be any known radiation source used for radiotherapy, including a device for providing an external beam to the patient or a radiation source introduced into the patient's body for brachytherapy. The radiation provided may be photon or ion based.

According to the invention at least one of the factors that are normally taken into account in the dose mimicking step S15 is introduced in the dose prediction step S13 to increase that chance that the predicted dose is close to an actually deliverable dose.

In a first preferred embodiment, the invention involves considering physical descriptors in the dose prediction stage, together with the physicality of the source of radiation. That is, the combined properties of the source of radiation and how it interacts with the patient tissue. The physical descriptors are given by the dose function $$d=f(x)$$

where x is the set of treatment parameters, d is the resulting dose distribution in the patient, and f is the mapping function from treatment parameters to dose. The physical descriptors of the patient may come from any suitable source, typically from a medical image of the patient taken at an earlier point in time or in connection with the treatment planning. The medical image may be, for example, a planning image acquired for the initial treatment planning, or a fraction image taken before the delivery of a fraction, or a combination of two or more such images.

As a first possible implementation, an approximation of the dose mapping function f(x) could be introduced as a non-trainable layer in the machine learning system. For this embodiment, the machine learning system is preferably a neural network, which in the case of photon radiotherapy planning is arranged to output a desired fluence instead of the desired dose, as is done conventionally. In this case, accordingly, the output S14 from the dose prediction step, would be a desired fluence map instead of a predicted dose distribution. The dose mimicking step S15 could in this case be adapted to work either on the dose distribution or on the fluence map, or on both.

A second possible implementation of the first embodiment would be to introduce a metric related to the difference between the output of the dose function and the dose, that is, |f(x)−d| as a penalty term part of the loss function for the machine learning system. The metric may, for example, be the absolute value of the difference, but any suitable metric may be used. For this second option, any optimization-based machine learning system could be used. Alternatively, a method based on a combination of machine learning and constraint satisfaction programming could be used. In this case d=f(x) would be imposed as a hard constraint in the machine learning system during training, so that the constraint would be an intrinsic part of the trained model.

In a second preferred embodiment, the invention involves considering machine constraints of the delivery system in the dose prediction stage. The machine constraints involve such factors as how much and how fast components of the delivery system, such as gantry and collimator leaves, can move. The machine constraints could be added to the optimization problem of any optimization-based machine learning system as an objective function or, preferably, as a constraint, to be treated analogously to the physics constraints discussed above.

The first and second preferred embodiments can be implemented independently of each other but can also be used together, to ensure that the predicted dose takes into account both the physicality of the patient and the technical constraints of the delivery system.

Figure 2:
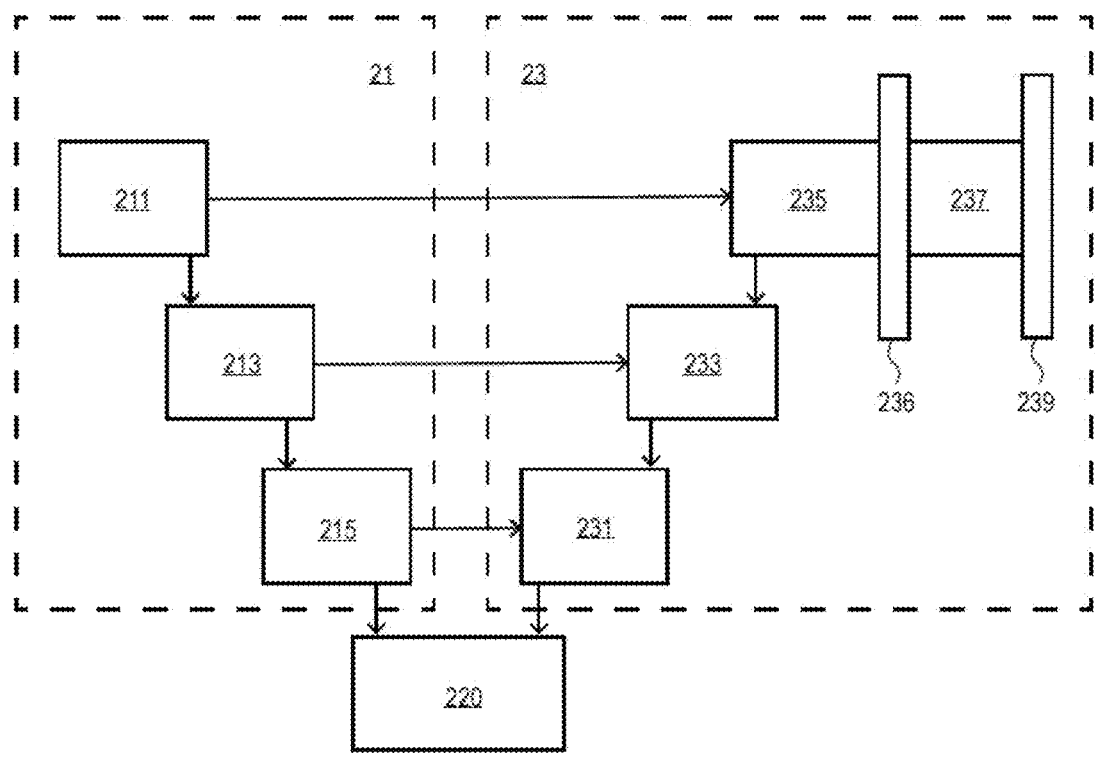
FIG. 2 illustrates the structure of a U-Net neural network adapted for use in an embodiment of the invention.

FIG. 2 illustrates a simplified architecture of a neural network known as a U-Net, adapted for use according to embodiments of the invention. The basic function of a U-Net is known to the skilled person and will only be discussed in general terms. As is common in the art, the U-Net comprises a number of layers; FIG. 2 shows a model with four layers. As will be known to the skilled person, the U-Net has a contracting path 21, the leftmost leg of the U and an expanding path 23, the rightmost leg of the U shape shown in FIG. 2. The contracting path 21 consists of repeated application of convolutions 211, 213, 215, each followed by a rectified linear unit (ReLU) and a max pooling operation, as will be known to the skilled person. During the contraction, the spatial information is reduced while feature information is increased. The fourth layer is the fully contracted layer 220. The expansive pathway 23 combines the feature and spatial information through a sequence of up-convolutions 231, 233, 235 and concatenations with high-resolution features from the contracting path 21. The uppermost layer 235 of the expanding path 23 includes a concatenation function and a convolution function as is common in the art, and the output of this according to embodiments of the invention will be a predicted dose 236. The predicted dose 236 is input to a non-trainable layer 237 arranged to calculate irradiation parameters 239 based on the predicted dose 236. The irradiation parameters 239 may be used to control dose delivery.

As explained above, input data to the machine learning model will include a medical image and structure data related to the patient.

Figure 3:
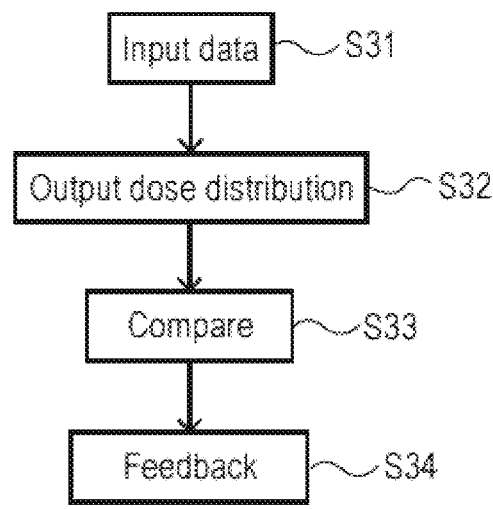
FIG. 3 is a flow chart of a method according to an embodiment of the invention.

FIG. 3 is a flow chart of a method of training the machine learning system according to embodiments of the invention. The training preferably comprises refining an optimization process, wherein the optimization procedure is based on an optimization problem comprising an optimization function related to at least one optimality criterion. In a first step S31, a set of input data is provided to a machine-learning system that is to be trained. The set of input data is related to a medical image of a patient, a structure data set, and a desired dose distribution dependent on patient geometry, determined on the basis of the medical image. According to embodiments of the invention, the set of input data also comprises at least one optimality criterion related to physical or technical restrictions that will affect the delivery of the treatment plan.

In step S32, the machine learning system produces an output based on the input data. In step S33, the output from step S32 is compared to a desired dose distribution already available and in step S34 the result of the comparison is fed to the machine-learning system as feedback.

The at least one optimality criterion may be related to the combined effect of the properties of the radiation source and the geometry of the patient. Alternatively, or in addition, the at least one optimality criterion may be related to the technical constraints of a delivery system to be used when delivering the treatment. Preferably, as shown in FIG. 2, the machine learning system includes a non-trainable layer based on a dose function for the patient and the machine learning system is arranged to output a predicted dose distribution or a set of irradiation parameters that can be used to generate a dose prediction for the patient to be used as input data to the dose mimicking stage.

Figure 4:
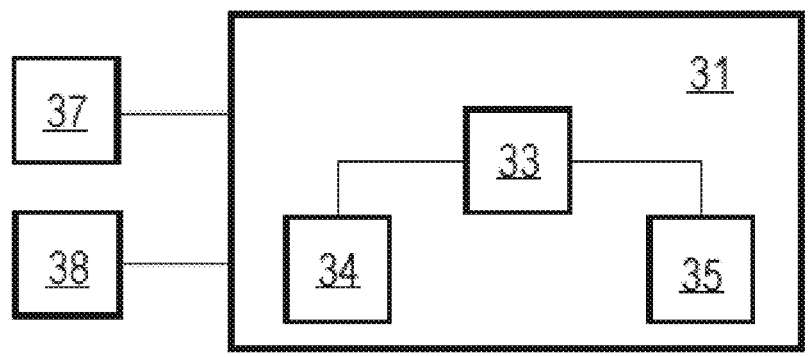
FIG. 4 is a schematic drawing of a computer system which may be used according to the invention.

FIG. 4 is a schematic representation of a computer system in which the inventive method may be performed. A computer 31 comprises a processor 33, a data memory 34 and a program memory 35. Preferably, a user input means 37, 38 is also present, in the form of a keyboard, a mouse, a joystick, voice recognition means or any other available user input means. The user input means 37, 38 may also be arranged to receive data from an external memory unit. It should be understood that FIG. 4 is only provided to illustrate different components that may be used to implement the method according to the invention and that the actual computer architecture can vary. One or more of the components, or the whole system, may be implemented in a cloud environment.

The data memory 34 typically comprises the necessary input data and the output data from the dose prediction step, as well as the treatment plan. The treatment plan may be generated in the computer 31, or received from another storage means in any way known in the art. As will be understood, the data memory 34 is only shown schematically. There may be several data memory units, each holding one or more different types of data, for example, one data memory for the input data, one for the dose distribution or irradiation parameters, etc.

The program memory 35 holds a machine learning system as discussed above and a dose mimicking program. As will be understood, the data memory 34 and/or program memory 35 are not necessarily part of the same computer as the processor 33, and may be located in any computer that is reachable from the processor 33, such as in a cloud environment

The invention claimed is:

1. A computer-based method for generating a radiotherapy treatment plan for a patient, the radiotherapy treatment plan comprising providing radiation to a patient from a radiation source, the computer-based method comprising:
generating, by using a machine learning system, a predicted dose distribution or a set of irradiation parameters that can be used to generate a dose prediction for the patient dependent on a patient geometry, based on a medical image and structure data comprising at least one delineated structure of the patient, wherein the machine learning system has been trained to consider a physicality of a delivery process including an interaction of the patient geometry and properties of the radiation source as at least one optimality criterion, and an output from the dose prediction is expressed as a predicted dose distribution or a set of irradiation parameters, or both; and
generating, by using the predicted dose distribution or the set of irradiation parameters, a deliverable treatment plan.

2. The computer-based method of claim 1, wherein the machine learning system has been trained to consider constraints of a system used for a delivery of the radiotherapy treatment plan.

3. The computer-based method of claim 1, wherein the machine learning system comprises a non-trainable layer based on a dose function for the patient and is arranged to output a fluence distribution for each beam, spot positions and weights for each beam and energy, or a set of brachy seed positions and dwell times, depending on a type of a radiotherapy, and/or a dose distribution.

4. The computer-based method of claim 1, wherein an optimization problem comprises at least one constraint related to the at least one optimality criterion.

5. The computer-based method of claim 1, wherein the machine learning system is a neural network that has been designed to consider at least one technical constraint of a delivery system to be used when delivering the radiotherapy treatment plan as the at least one optimality criterion.

6. A computer program product comprising:
a non-transitory computer readable storge medium having program instructions embodied therewith, which, when run in a computer, cause the computer to perform the computer-based method of claim 1.

7. A computer system comprising:
a processor, and
a program memory,
wherein the program memory comprises a computer program code configured to, when executed by the processor, causes the processor to perform the computer-based method of claim 1.

8. A method for training a machine learning system for use in radiotherapy treatment planning, comprising:
providing a set of input data related to a medical image of a patient, structure date comprising at least one delineated structure of the patient, and a desired dose distribution dependent on a patient geometry, determined on a basis of the medical image of the patient to a machine learning system,
comparing an output from the machine learning system to the desired dose distribution, and feeding a result of the comparing to the machine learning system, wherein the set of input data further comprises at least one optimality criterion related to physical or technical restrictions that will affect a delivery of a treatment plan, and
training the machine learning system to consider the at least one optimality criterion related to physical or technical restrictions that will affect the delivery of the treatment plan.

9. The method of claim 8, wherein the at least one optimality criterion is related to a combined effect of properties of a radiation source and the patient geometry of the patient.

10. The method of claim 9, wherein the training comprises refining an optimization process, wherein the optimization process is based on an optimization problem comprising an optimization function related to the at least one optimality criterion.

11. The method of claim 8, wherein the machine learning system includes a non-trainable layer based on a dose function for the patient, and the machine learning system is arranged to output a predicted dose distribution or a set of irradiation parameters that can be used to generate a dose prediction for the patient to be used as input data to a dose mimicking stage.

12. The method of claim 8, wherein the at least one optimality criterion is related to technical constraints of a delivery system to be used when delivering the treatment plan.

13. A computer program product comprising:
a non-transitory computer readable storge medium having program instructions embodied therewith, which, when run in a computer, cause the computer to perform the method of claim 8.

14. A computer system comprising:
a processor, and
a program memory,
wherein the program memory comprises a computer program code configured to, when executed by the processor, causes the processor to perform the method of claim 8.

* * * * *